US007822466B2

(12) United States Patent
Stoianovici et al.

(10) Patent No.: US 7,822,466 B2
(45) Date of Patent: Oct. 26, 2010

(54) ROBOT FOR COMPUTED TOMOGRAPHY INTERVENTIONS

(75) Inventors: Dan Stoianovici, Baltimore, MD (US); Dumitru Mazilu, Lutherville, MD (US); Louis R. Kavoussi, Lotherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 843 days.

(21) Appl. No.: 10/423,028

(22) Filed: Apr. 25, 2003

(65) Prior Publication Data

US 2010/0240989 A1 Sep. 23, 2010

Related U.S. Application Data

(60) Provisional application No. 60/375,559, filed on Apr. 25, 2002.

(51) Int. Cl.
*A61B 5/05* (2006.01)
(52) U.S. Cl. .................. 600/427; 600/229; 600/407; 600/424; 606/130; 901/15; 901/41; 74/479.01
(58) Field of Classification Search .................. 600/229, 600/407, 417, 424; 901/15, 41; 606/130; 74/479.01; 5/601
See application file for complete search history.

(56) References Cited

U.S. PATENT DOCUMENTS

| 4,068,763 | A | 1/1978 | Fltecher et al. |
| 4,098,001 | A | 7/1978 | Watson |
| 4,149,278 | A | 4/1979 | Wiker et al. |
| 4,355,469 | A | 10/1982 | Nevins et al. |
| 4,409,736 | A | 10/1983 | Seltzer |
| 4,477,975 | A | 10/1984 | De Fazio et al. |
| 4,501,522 | A | 2/1985 | Causer et al. |
| 4,537,557 | A | 8/1985 | Whitney |
| 4,556,203 | A | 12/1985 | Rourke et al. |
| 4,583,538 | A | * | 4/1986 | Onik et al. .................. 606/130 |
| 4,653,509 | A | * | 3/1987 | Oloff et al. .................. 600/562 |
| 4,666,361 | A | | 5/1987 | Kitabatake et al. |
| 4,668,222 | A | * | 5/1987 | Poirier ....................... 604/175 |

(Continued)

OTHER PUBLICATIONS

Cleary et al., Image-Guided Robotic Delivery System for Precise Placement of Therapeutic Agents, 2001, Journal of Controlled Release 74: pp. 363-368.*

(Continued)

*Primary Examiner*—Brian Casler
*Assistant Examiner*—James Kish
(74) *Attorney, Agent, or Firm*—Arent Fox LLP

(57) ABSTRACT

A system and method for CT guided instrument targeting including a radiolucent instrument driver; a robot and a control box. The robot includes a robotic module that positions the radiolucent driver about two directions coincident a predetermined point. The control device is connected to the robot and the radiolucent instrument driver. The control driver sends a robot control signal to the robot that causes the robotic module to place the radiolucent instrument driver in a desired orientation with respect to the predetermined point. After the radiolucent instrument driver is in the desired orientation, the control device sends a driver control signal to the radiolucent instrument driver that causes the radiolucent driver to insert a medical instrument or device through the predetermined point to a location proximate a target point in a patient.

25 Claims, 11 Drawing Sheets

U.S. PATENT DOCUMENTS

| | | | |
|---|---|---|---|
| 4,970,448 A | | 11/1990 | Torii et al. |
| 5,078,140 A | * | 1/1992 | Kwoh .......................... 600/417 |
| 5,086,401 A | * | 2/1992 | Glassman et al. ........... 700/259 |
| 5,142,930 A | * | 9/1992 | Allen et al. .................... 74/469 |
| 5,147,372 A | * | 9/1992 | Nymark et al. ............. 600/429 |
| 5,207,114 A | | 5/1993 | Salisbury et al. |
| 5,280,427 A | * | 1/1994 | Magnusson et al. ......... 600/407 |
| 5,305,653 A | | 4/1994 | Ohtani et al. |
| 5,397,323 A | * | 3/1995 | Taylor et al. ................. 606/130 |
| 5,515,478 A | | 5/1996 | Wang |
| 5,537,702 A | * | 7/1996 | Brown-Milants et al. ........ 5/632 |
| 5,549,644 A | * | 8/1996 | Lundquist et al. ............. 604/22 |
| 5,572,999 A | | 11/1996 | Funda et al. |
| 5,630,431 A | | 5/1997 | Taylor |
| 5,647,554 A | | 7/1997 | Ikegami et al. |
| 5,772,580 A | | 6/1998 | Utsui et al. |
| 5,792,135 A | | 8/1998 | Madhani et al. |
| 5,806,518 A | | 9/1998 | Mittelstadt |
| 5,817,084 A | | 10/1998 | Jensen |
| 5,876,325 A | | 3/1999 | Mizuno et al. |
| 5,907,664 A | | 5/1999 | Wang et al. |
| 5,957,933 A | * | 9/1999 | Yanof et al. .................. 606/130 |
| 6,000,297 A | * | 12/1999 | Morimoto et al. ........ 74/479.01 |
| 6,047,610 A | | 4/2000 | Stocco et al. |
| 6,055,449 A | | 4/2000 | Navab |
| 6,105,454 A | | 8/2000 | Bacchi et al. |
| 6,206,890 B1 | * | 3/2001 | Truwit ......................... 606/130 |
| 6,245,028 B1 | * | 6/2001 | Furst et al. ................... 600/568 |
| 6,246,200 B1 | | 6/2001 | Blumenkranz et al. |
| 6,246,898 B1 | * | 6/2001 | Vesely et al. ................. 600/424 |
| 6,267,022 B1 | | 7/2001 | Suzuki |
| 6,408,224 B1 | | 6/2002 | Okamoto et al. |
| 6,558,107 B1 | | 5/2003 | Okuno |
| 6,665,554 B1 | * | 12/2003 | Charles et al. ............... 600/427 |
| 6,675,671 B1 | | 1/2004 | Jokiel et al. |
| 6,676,669 B2 | * | 1/2004 | Charles et al. ............... 606/130 |
| 6,785,572 B2 | * | 8/2004 | Yanof et al. .................. 600/427 |
| 6,889,119 B2 | | 5/2005 | Riff et al. |

OTHER PUBLICATIONS

Stoianovici et al., A Modular Surgical Robotic System for Image Guided Percutaneous Procedures, 1998, MICCAI, pp. 404-410.*

Taylor et al., "A Steady-Hand Robotic System for Microsugrical Augmentation." Dec. 1999. International Journal of Robotics Research. vol. 18, No. 12. pp. 1201-1210.*

M.H. Loser et al.; "Visual Servoing for Automatic and Uncalibrated Percutaneous Procedures"; Proc. SPIE vol. 3976; pp. 270-281; Medical Imaging 2000: Image Display and Visualization; Seong K. Mun; Ed., published Apr. 2000; 12 pages.

N. Navab et al.; "Visual Servoing for Automatic and Uncablibrated Needle Placement for Percutaneous Procedures", Proc. Of IEEE Conf. On Computer Vision and Pattern Recognition, Jun. 13-15, 2000: Hilton Head Island, South Carolina, USA, 8 pages.

* cited by examiner

Front and Side Views of the Robot Mounted on the CT Scanner

ROBOT FOR COMPUTED TOMOGRAPHY INTERVENTIONS

CROSS REFERENCE TO RELATED APPLICATION

This application claims priority to Provisional Patent Application No. 60/375,559, entitled TRACKER ROBOT FOR CT-GUIDED INTERVENTIONS, filed on Apr. 25, 2002, the contents of which are incorporated herein by reference.

STATEMENT REGARDING FEDERALLY SPONSORED RESEARCH

This work was partially supported by grant No. DAMD17-99-1-9022 from the U.S. Army Medical Research Acquisition Activity (USAMRAA) and by grant No 1R21CA088232-01A1 from the National Cancer Institute (NCI). This work was also supported in part by the National Science Foundation under Cooperative Agreement EEC 9731478, "Engineering Research Center for Computer-Integrated Surgical Systems and Technology."

BACKGROUND OF THE INVENTION

1. Field of the Invention

The present invention relates to robotic devices and methods for instrument targeting. In particular, the invention relates to systems and methods for computer assisted image-based instrument targeting used in computed tomography (CT) guided interventions.

2. Description of the Related Art

Minimally invasive and noninvasive procedures for surgery are gaining increased popularity mainly due to reduced trauma to patients and improved recovery time. One of the main problems encountered in minimally invasive procedures is, in contrast to open surgical procedures, a dramatic reduction in the surgeon's visual ability. Accordingly, radiological, ultrasonic, and magnetic resonance imaging techniques are employed to map anatomical geometry during intra-operative procedures.

CT and CT fluoroscopy (CTF) are among these imaging techniques. Systems and methods for using CT and CTF in guided interventions have been developed.

CT interventions have been further enabled by the development of CT CTF imagers [Daly B, Krebs T L, Wong-You-Cheong J J, Wang S S: Percutaneous abdominal and pelvic interventional procedures using CT fluoroscopy guidance. AJR (1999) 173:637-644 and Gianfelice D, Lepanto L, Perreault P, Chartrand-Lefebvre C, Milette P C: Value of CT fluoroscopy for percutaneous biopsy procedures. JVIR 2000 (2000) 11:879-884], which in addition to classic CT capabilities, allow for fluoro-imaging of a CT slice. The radiologist manually orients and inserts the instrument while keeping it in the fluoro slice by observing the fluoro monitor [Silverman S G, Tuncali K, Adams D F, Nawfel R D, Zou K H, Judy P F: CT fluoroscopy-guided abdominal interventions: techniques, results, and radiation exposure. Radiology (1999) 212:673-681]. In experienced hands the procedure is fast and normally successful. [Kato R, Katada K, Arno H, Suzuki S, Ida Y, Koga S.: Radiation dosimetry at CT fluoroscopy: physician's hand dose and development of needle holders. Radiology (1996) 201:576-578]. The major limitations of CTF interventions are the relatively high radiation exposure [Gianfelice D, Lepanto L, Perreault P, Chartrand-Lefebvre C; Milette P C: Effect of the learning process on procedure times and radiation exposure for ct fluoroscopy-guided percutaneous biopsy procedures. JVIR (2000) 11:1217-1221; Nawfel R D, Judy P F, Silverman S G, Hooton S, Tuncali K, Adams D F: Patient and personnel exposure during ct fluoroscopy-guided interventional procedures. Radiology (2000) 216:180-184; and Nickoloff E L, Khandji A, Dutta A: Radiation doses during ct fluoroscopy. Health Physics (2000) 79:675-681], the constraint of operating in a CT slice [Gianfelice D, Lepanto L, Perreault P, Chartrand-Lefebvre C, Milette P C: Value of CT fluoroscopy for percutaneous biopsy procedures. JVIR 2000 (2000) 11:879-884 and Nawfel R D, Judy P F, Silverman S G, Hooton S, Tuncali K, Adams D F: Patient and personnel exposure during ct fluoroscopy-guided interventional procedures. Radiology (2000) 216:180-184], and the reduced resolution of the CTF compared to the CT images [Daly B, Krebs T L, Wong-You-Cheong J J, Wang S S: Percutaneous abdominal and pelvic interventional procedures using CT fluoroscopy guidance. AJR (1999) 173:637-644 and Patriciu A, Mazilu D, Stoianovici D, Stanimir A, Susil R, Masamune K, Fitchinger G, Taylor R H, Anderson J, Kavoussi L R: CT-Guided Robotic Prostate Biopsy, (2000), 18th World Congress on Endourology & SWL, September 2000, Sao Paulo, Brazil].

CT fluoroscopy (CTF) offers many advantages to performing interventional procedures. With CT fluoroscopy the trajectory of a needle can be tracked in real time allowing the physician to make adjustments as necessary. This advance has made procedures faster with equivalent or better success rates. Gianfelice et al. reported faster biopsy procedure times with mean times significantly declining from 43 minutes with conventional CT to 28 minutes with CTF, and procedure success rates increasing from 88% to 94% [Gianfelice D, Lepanto L, Perreault P, Chartrand-Lefebvre C, Milette P C. Value of ct fluoroscopy for percutaneous biopsy procedures. *JVIR* 2000; 11:879-884]. Likewise, Silverman et al. reported mean needle placement times significantly decreasing from 36 minutes with conventional CT to 29 minutes with CTF and with equivalent success rates between the two modalities [Silverman S G, Tuncali K, Adams D F, Nawfel R D, Zou K H, Judy P F. CT fluoroscopy-guided abdominal interventions: techniques, results, and radiation exposure. *Radiology* 1999; 212:673-681]

CTF has made interventional procedures faster with equivalent or better success rates [Gianfelice D, Lepanto L, Perreault P, Chartrand-Lefebvre C, Milette P C. Value of ct fluoroscopy for percutaneous biopsy procedures. JVIR 2000; 11:879-884 and Silverman S G, Tuncali K, Adams D F, Nawfel R D, Zou K H, Judy P F. CT fluoroscopy-guided abdominal interventions: techniques, results, and radiation exposure. Radiology 1999; 212:673-681]. However, the major limitation to the modality is the relatively high radiation exposure to patient and physician [Nawfel R D, Judy P F, Silverman S G, Hooton S, Tuncali K, Adams D F. Patient and personnel exposure during ct fluoroscopy-guided interventional procedures. Radiology 2000; 216:180-184 and Kato R, Katada K, Anno H, Suzuki S, Ida Y, Koga S. Radiation dosimetry at ct fluoroscopy: physician's hand dose and development of needle holders. Radiology 1996; 201:576-578]. Robots have been used in surgery to solve problems of holding and controlling instruments [Paulson E K, Sheafor D H, Enterline D S, McAdams H P, Yoshizumi T T. CT fluoroscopy-guided interventional procedures: techniques and radiation dose to radiologists. Radiology 2001; 2-20:161-167; Kavoussi L R; Moore R G, Adams J B, Partin A W. Comparison of robotic versus human laparoscopic camera control. J Urol 1995 December; 154(6):2134-6; Fadda M, Marcacci M, Toksvig-Larsen S, Wang T, Meneghello R. Improving accuracy of bone resections using robotics tool holder and a high speed milling cutting tool. *J Med Eng Technol* 1998 November-December; 22(6):280-4; and Koyama H, Uchida T, Funakubo H, Takakura K, Fankhauser H. Development of a new microsurgical robot for stereotactic neurosurgery. Stereotact Funct Neurosurg 1990; 54:462-467].

The major limitation of CTF is the relatively high radiation exposure to patient and physician. In order to make the real time adjustments in needle trajectory the physician's hand is in proximity to the scanning plane. Physician hand exposure has been theoretically and empirically determined to be approximately 2 mGy per procedure [Nawfel R D, Judy P F, Silverman S G, Hooton S, Tuncali K, Adams D F. Patient and personnel exposure during ct fluoroscopy-guided interventional procedures. *Radiology* 2000; 216:180-184]. Kato et al. have calculated that on the basis of an annual dose limit of 500 mSv for the hands, a physician with continuous hand exposure would be limited to performing only four CTF procedures per year. As such, a number of procedural techniques and shields have been suggested to minimize radiation exposures. Kato et al. and Daly et al. have used needle holders and Nawfel et al. have; used lead drapes all to minimize hand exposure [Kato R, Katada K, Anno H, Suzuki S, Ida Y, Koga S. Radiation dosimetry at ct fluoroscopy: physician's hand dose and development of needle holders. *Radiology* 1996; 201:576-578; Nickoloff E L, Khandji A, Dutta A. Radiation doses during ct fluoroscopy. *Health Physics* 2000; 79:675-681; and Daly B, Krebs T L, Wong-You-Cheong J J, Wang S S. Percutaneous abdominal and pelvic interventional procedures using ct fluoroscopy guidance. *AJR* 1999; 173:637-644]. Others have noted that experience and training may lead to a reduction in exposure [Gianfelice D, Lepanto L, Perreault P, Chartrand-Lefebvre C, Milette P C. Effect of the learning process on procedure times and radiation exposure for ct fluoroscopy-guided percutaneous biopsy procedures. *JVIR* 2000; 11:1217-1221]. Paulson et al. recently reported lowering radiation exposure by lowering mA and taking intermittent spot images during the procedure [Paulson E K, Sheafor D H, Enterline D S, McAdams H P, Yoshizumi T T. CT fluoroscopy-guided interventional procedures: techniques and radiation dose to radiologists. *Radiology* 2001; 2-20:161-167]. Intermittent "spot check" images has gained greater acceptance as it generally can allow successful completion of the intervention with significant reduction of radiation exposure.

A number of procedural techniques [Nawfel R D, Judy P F, Silverman S G, Hooton S, Tuncali K, Adams D F: Patient and personnel exposure during ct fluoroscopy-guided interventional procedures. Radiology (2000) 216:180-184], shields [Nickoloff E L, Khandji A, Dutta A: Radiation doses during ct fluoroscopy. Health Physics (2000) 79:675-681], and needle holders [Bishoff J T, Stoianovici D, Lee B R, Bauer J, Taylor R H, Whitcomb L L, Cadeddu J A, Chan D, Kavoussi L R: RCM-PAKY: Clinical Application of a New Robotic System for Precise Needle Placement, (1998), Journal of Endourology, 12:82 and Stoianovici D, Cadeddu J A, Demaree R D, Basile H A, Taylor R H, Whitcomb L L, Sharpe W, Kavoussi L R: An Efficient Needle Injection Technique and Radiological Guidance Method for Percutaneous Procedures, (1997), LNCS, Springer-Verlag, 1205:295-298] have been proposed to reduce radiation exposure. Robotic systems have also been pursued for their unique capability of collectively eliminating the limitations of the manual procedure [Stoianovici D: Robotic Surgery, (2000) World Journal of Urology, 18:4:289-295]. Unlike manual interventions, robotic CT guided procedures are not necessarily limited to the use-of CTF [Patriciu A, Stoianovici D, Whitcomb L L, Jarrett T, Mazilu D, Stanimir A, Iordachita I, Anderson J, Taylor R, Kavoussi L R, (2000), "Motion-Based Robotic Instrument Targeting Under C-Arm Fluoroscopy", LNCS, Springer-Verlag, Vol. 1935, pp. 988-998 and Solomon S, Patriciu A, Masamune K, Whitcomb L, Taylor R H, Kavoussi L, Stoianovici D, 2001, "CT Guided Robotic Needle Biopsy: A Precise Sampling Method Minimizing Radiation Exposure", Radiology, in press]. This approach, however, requires specialized robotic hardware, image registration, and guidance algorithms.

Robots have been introduced into the operating room to hold and move instruments precisely. Robots allow greater precision, allow greater accuracy, and lack tremor when compared to humans [Kavoussi L R; Moore R G, Adams J B, Partin A W. Comparison of robotic versus human laparoscopic camera control. *J Urol* 1995 December; 154(6):2134-6 and Fadda M, Marcacci M, Toksvig-Larsen S, Wang T, Meneghello R. Improving accuracy of bone resections using robotics tool holder and a high speed milling cutting tool. *J Med Eng Technol* 1998 November-December; 22(6):280-4]. Neurosurgeons have used robots to perform stereotactic biopsies using previously acquired CT images [Koyama H, Uchida T, Funakubo H, Takakura K, Fankhauser H. Development of a new microsurgical robot for stereotactic neurosurgery. *Stereotact Funct Neurosurg* 1990; 54:462-467; Kwoh Y S, Hou J, Jonckheere E A, Hayati S. A robot with improved absolute positioning accuracy for ct guided stereotactic brain surgery. *IEEE Trans Biomed Eng* 1988; 35:153-160; and Fankhauser H, Glauser D, Flury P, Piguet Y, Epitaux M, Favre J, Meuli R A. Robot for ct-guided stereotactic neurosurgery. *Stereotact Fund Neurosurg* 1994; 63:93-98]. Cardiac surgeons use robots to translate gross movements on a magnified image into fine robotic movements in the body [Autschbach R, Onnasch J F, Falk V, Walther T, Kruger M, Schilling L O, Mohr F W. The Leipzig experience with robotic valve surgery. *J Card Surg.* 2000-January-February; 15(1):82]. One of the advantages of robots capitalized on in telesurgical applications is the fact that the surgeon does not need to be in the same location as the patient [Lee B R, Png D J,—Liew L, Fabrizio M, Li M K, Jarrett J W, Kavoussi L R. Laparoscopic telesurgery between the United States and Singapore. *Ann Acad Med Singapore* 2000 September; 29(5): 665-8]. Multiple reports of remote surgery exist [Link R E, Schulam P G, Kavoussi L R. Telesurgery. Remote monitoring and assistance during laparoscopy. *Urol Clin North Am* 2001 February; 28(I):177-88; Cheah W K, Lee B, Lenzi J E, Goh P M. Telesurgical laparoscopic cholecystectomy between two countries. *Surg Endosc.* 2000 November; 14(11):1085; and Marescaux J, Smith M K, Folscher D, Jamali F, Malassagne B, Leroy J. Telerobotic Laparoscopic Cholecystectomy: Initial Clinical Experience With 25 Patients. *Ann Surg* 2001 July; 234(1):1-7]. This advantage of operating remotely may be used to limit radiation exposure in CTF guided interventional procedures.

Specialized algorithms have been proposed for robot-image registration and/or instrument guidance [Stoianovici D: Robotic Surgery, (2000) World Journal of Urology, 18:4:289-295]. A servoing method using the procedure needle as a marker under CT-fluoroscopy was reported by Loser and Navab [Loser M-I, Navab N: A new robotic system for visually controlled percutaneous interventions under CT fluoroscopy, MICCAI 1999, LNCS, Springer-Verlag (2000) 1935: 887-896]. Susil et al. [Susil R C, Anderson J, Taylor R H: A Single Image Registration Method for CT Guided Interventions, LNCS, Springer-Verlag (1999) 1679:798-808] reported a registration method using a localization device (a modified Brown-Roberts-Wells frame [Brown R A, Roberts T S, Osborne A G: Stereotaxic frame and computer software for CT directed Neurosurgical localization. Invest. Radiol. (1980), 15: 308-312]) attached to the robot's end-effector, which was further perfected by Masamune [Masainune K, Patriciu A, Stoianovici D, Susil R, Taylor R H, Fichtinger G, Kavoussi L R, Anderson J, Sakuma I, Dohi T: Development of CT-PAKY frame system—CT image guided Needle puncturing manipulator and a single slice registration for urological surgery, Proc. 8th annual meeting of JSCAS, Kyoto 1999:89-90] and Patriciu [Fichtinger G, DeWeese T L, Patriciu A, Tanacs A, Mazilu D, Anderson J H, Masamune K, Taylor R H, Stoianovici D, (2001), "System For Robotically Assisted Prostate Biopsy And Therapy With IntraOperative CT Guidance", Academic Radiology, in press and Patriciu A, Mazilu D, Stoianovici D, Stanimir A, Susil R, Masamune K, Fitchinger G, Taylor R H, Anderson J, Kavoussi L R: CT-Guided Robotic Prostate Biopsy, (2000), 18th World Congress on Endourology & SWL, September 2000, Sao Paulo, Brazil].

Initially, investigators used industrial robots [Kwoh Y S, Hou J, Jonckeere E A, H&yati S:—A robot with improved absolute positioning accuracy for CT guided stereotactic brain surgery, IEEE Transactions on Biomedical Engineering, 35(2), pp. 153-160, 1988] to prove the feasibility of robotic CT-guided procedures. Specialized image-guided robots have then been developed following the innovative trend of surgical robotics in general [Stoianovici D: Robotic Surgery, (2000) World Journal of Urology, 18:4:289-295].

The PinPoint™ system manufactured by Marconi Medical Systems is an example of a passive system that highly enhances CT navigation capabilities [Cook A, Ravenna O, Cook A, Yanof J, Cavnah P, Hines J, Chaturvedi A: Interactive Computer User Interface for Planning Robotic Assisted Interventions, Radiology, 1999, Vol. 213, pp. 577]. PinPoint is a frameless stereotactic arm using joint encoders to provide the position of its end-effector instrument with respect to the CT gantry thus allowing for-the visualization of the instrument in the CT image space. The PinPoint arm can also be locked at the desired location to serve as a guide for needle placement.

Minerva (Laboratory of Microengineering at the Swiss Federal Institute of Technology in Lausanne, Switzerland) is a CT-guided, multi-function neurosurgical robot [Fankhauser H, Glauser D, Flury P, Piguet Y, Epitaux M, Favre J, Meuli R A: Robot for CT-guided Stereotactic Neurosurgery, Stereotact Funct Neurosurg, 63(1-4), 93-8]. It operates inside a CT gantry with free longitudinal movement allowing cranial scans at any level. Under the physician's remote control, Minerva can manipulate two instruments in addition to the tool for automatic penetration of the skin, skull, and meninges [Glauser D, Fankhauser H, Epitaux M, Hefti J L, Jaccottet A: Neurosurgical robot Minerva—first results and current developments. J Image Guid Surg, 1(5), 266-72].

Another neurosurgical robot, NeuroMate™ (Integrated Surgical Systems, Davis, C A), originally developed at the University 6.f Grenoble, France [Benabid A L, Cinquin P, Lavalle S, Le Bas J F, Demongeot J, de Rougemont F: Computer-driven robot for stereotactic surgery connected to CT scan and magnetic resonance imaging. Technological design and preliminary results. Appl Neurophysiol, 50(1-6), 153-4 and Benabid A L, Lavallee S, Hoffmann D, Cinquin P, Demongeot J; Danel F: Potential use of robots in endoscopic neurosurgery. Acta Neurochir Suppl, 54, 93-7] is a frameless stereotactic system capable of carrying-out surgical procedures under image-guided remote physician control.

The components of many other surgical robot designs (such as the Intuitive Surgical daVinci™ robot [Blumenkranz S J, Rosa D J, "Manipulator Positioning Linkage for Robotic Surgery", U.S. Pat. No. 6,246,200, Jun. 12, 2001]) are based on the Remote Center of Motion (RCM) principle [Taylor R H, Funda J, Grossman D D, Karidis J P, LaRose D A, "Remote Center-of Motion Robot for Surgery", U.S. Pat. No. 5,397, 323, Mar. 14, 1995] invented by Taylor in 1995 and originally implemented on the LARS robot for laparoscopy developed at IBM [Taylor R H, Funda J, Eldridge B, Gruben K, LaRose D, Gomory S, Talamini M, Kavoussi L R, Anderson-J, (1995): "A Telerobotic Assistant for Laparoscopic Surgery", IEEE Engineering in Medicine and Biology Magazine, Vol. 14, pp. 279-287]. The RCM is perhaps the most common architecture used in surgical robotics [Stoianovici D: Robotic Surgery, (2000) World Journal of Urology, 18:4:289-295]. An example of an RCM mechanism is the prototype surgical robot designed for needle alignment inside a CT gantry reported in 1999 by Loser and Navab [Loser M-I, Navab N: A new robotic system for visually controlled percutaneous interventions under CT fluoroscopy, MICCAI 1999, LNCS, Springer-Verlag (2000) 1935:887-896]. The robot presents a small distal part made of radiolucent materials implementing a rigid-link parallelogram RCM. This is capable of actively orienting a procedure needle about the fixed location of its tip. The investigators derived a visual servoing algorithm for needle orientation. A needle guide is used for trajectory enforcement and insertion is performed manually.

Another RCM based experimental robot designed for Neuro-CT interventions was developed in 1998 by Masamune et al. [Masamune K, Ji L H, Suzuki M, Dohi T, Iseki H, Takakura K: A newly developed stereotactic robot with detachable driver for neurosurgery, Proc. MI CCAI 1998, pp. 215-222, 1998] at the University of Tokyo evolving from Dohi's 1993 design [Yamauchi Y, Ohta Y, Dohi T, Kawamura H, Tanikawa T, Iseki H: A needle insertion Manipulator for X-Ray CT image guided neurosurgery, J. of LST, vol. 5-4, 814-821, 1993]. This is a special RCM construction using a goniometer arc and a second revolute axis pointing towards its center. The system has a relatively small size and mounts on the mobile table of the CT scanner.

Our URobotics Laboratory [Stoianovici D, (2002): "URobotics—Urology Robotics at Johns Hopkins", Computer Aided Surgery, in press] has reported the development of three modular robotic components and two image registration/targeting methods related to X-Ray guided operations. A radiolucent needle driver PAKY [Cadeddu J A, Stoianovici D, Chen R N, Moore R G, Kavoussi L R: Stereotactic mechanical percutaneous renal access, (1998), Journal of Endourology, 12:2:121-126 and Stoianovici D, Cadeddu J A, Demaree R D, Basile H A, Taylor R H, Whitcomb L L, Sharpe W, Kavoussi L R: An Efficient Needle Injection Technique and Radiological Guidance Method for Percutaneous Procedures, (1997), LNCS, Springer-Verlag, 1205:295-298] was reported in 1997, the RCM robot reported in 1998 is a small surgical robot operating on the RCM principle [Stoianovici D, Whitcomb L L, Anderson J H, Taylor R H, Kavoussi L R: A Modular Surgical Robotic System for Image Guided Percutaneous Procedures, (1998) LNCS, Springer-Verlag, 1496: 404-410], and the G_ARM [Lerner, G, Stoianovici D, Whitcomb, L, L, Kavoussi L, R, (1999), "A Passive Positioning and Supporting Device for Surgical Robots and Instrumentation", LNCS, Springer-Verlag, Vol. 1679, pp. 1052-1061] reported in 1999 is a sturdy passive positioning arm In 2000 we used the PAKY-RCM-G_ARM system with a new fluoroservoing algorithm [Patriciu A, Stoianovici D, Whitcomb L L, Jarrett T, Mazilu D, Stanimir A, lordachita I, Anderson J, Taylor R, Kavoussi L R, (2000), "Motion-Based Robotic Instrument Targeting Under C-Arm Fluoroscopy", LNCS, Springer-Verlag, Vol. 1935, pp. 988-998] for percutaneous renal access under C-Arm guidance. In 2001 we reported a laser based registration method [Patriciu A, Solomon S, Kavoussi L R, Stoianovici D, (2001): "Robotic Kidney and Spine Percutaneous Procedures Using a New Laser-Based CT Registration Method", LNCS, Vol. 2208, pp. 249-258] for robotic CT interventions and implemented it on the PAKY-RCM robot. With this system we performed a comprehensive clinical study [Solomon S, Patriciu A, Masamune K, Whitcomb L, Taylor R H, Kavoussi L, Stoianovici D, 2001, "CT Guided Robotic Needle Biopsy: A Precise Sampling Method Minimizing Radiation Exposure", Radiology, in press] of kidney, spine, liver, and lung procedures of biopsies and radio-frequency (RF) ablation.

Thus, there is a need for new and improved robot systems and methods that take advantage of commonly available imaging technology and solve problems with the prior art.

SUMMARY OF THE INVENTION

A system and method for CT guided instrument targeting including a radiolucent instrument driver; a robot and a control box. The robot includes a robotic module that positions the radiolucent driver about two directions coincident a predetermined point. The control device is connected to the robot and the radiolucent instrument driver. The control driver sends a robot control signal to the robot that causes the robotic module to place the radiolucent instrument driver in a desired orientation with respect to the predetermined point. After the radiolucent instrument driver is in the desired orientation, the control device sends a driver control signal to the radiolucent instrument driver that causes the radiolucent driver to insert a medical instrument or device through the predetermined point to a location proximate a target point in a patient.

A robotic system for computed tomorgraphy (CT) guided operations includes a support mountable to a CT table. A XYZ module is carried by the support. A passive arm is connected to the XYZ module. A RCM robot module is connected to the passive arm. A PAKY radiolucent needle driver is carried and positioned by the robot module. A control device controls the XYZ module, the needle driver and the robot module. The control device outputs a first signal to the XYZ module that controls the position of the XYZ module, a second signal to the robot module that controls the position of the needle driver and a third signal to the needle driver that controls the needle driver.

A system for computed tomography (CT) operations includes position means for positioning a tip of a medical device at an insertion point. Registration means registers the medical device. Orientating means orientates the medical device to an orientation required to insert the medical device through the insertion point and position the tip of the medical device proximate a target. Inserting means inserts the medical device through the insertion point to a point where the tip of the medical device is proximate the target.

A method for computed tomography guided operations includes: positioning a tip of a medical device at an insertion point; registering the medical device; orientating the medical device to an orientation required to insert the medical device through the insertion point and position the tip of the medical device proximate a target; and inserting the medical device through the insertion point to a position where the tip of the medical device is proximate the target.

BRIEF DESCRIPTION OF THE DRAWINGS

The objects and features of the invention will be more readily understood with reference to the following description and the attached drawings, wherein:

FIG. 7A shows the needle in the plane of the laser-with reflection on the shaft (arrow)

FIGS. 8A and B show the two images sent to the computer workstation;

FIG. 8A is used by the physician to indicate the tip of the needle at the skin and the holder of the needle; FIG. 8B is used to indicate the target; and FIGS. 9A, B, and C show examples of three CT interventional procedures. FIG. 9A shows the robot positioned for a percutaneous biopsy. FIG. 9B shows the robot positioned for an RF ablation, FIG. 9C shows the robot positioned for a nephrostomy tube placement. The physician in the room is finishing the procedure with the working site outside of the gantry.

DETAILED DESCRIPTION OF THE PREFERRED EMBODIMENT

Description of the Robot

The preferred embodiment of the present invention uses PAKY and RCM robotic modules assembled in a CT-specific configuration and will undergo clinical trials at Georgetown University Medical Center [Cleary K, Stoianovici D, Watson V, Cody R, Hum B, and Lindisch D: "Robotics for pereutaneous spinal procedures: initial report," Computer Assisted Radiology and Surgery (CARS) 2000, Elsevier, 128-33]. One component of the preferred system is the PAKY-RCM robot developed at the URobotics Laboratory at Johns Hopkins. This robot includes the PAKY needle driver (Percutaneous Access of the Kidney) and the RCM (Remote Center of Motion) robot [Stoianovici, D., Witcomb, L. L., Anderson, J. H., Taylor, R. H., Kavoussi, L. R.: "A Modular Surgical Robotic System for Image Guided Percutaneous Procedures", 1998 MICCAI, Lecture Notes in Computer Science, Springer-Verlag, Vol. 1496, pp. 404-410, 1998].

Figure 1A:
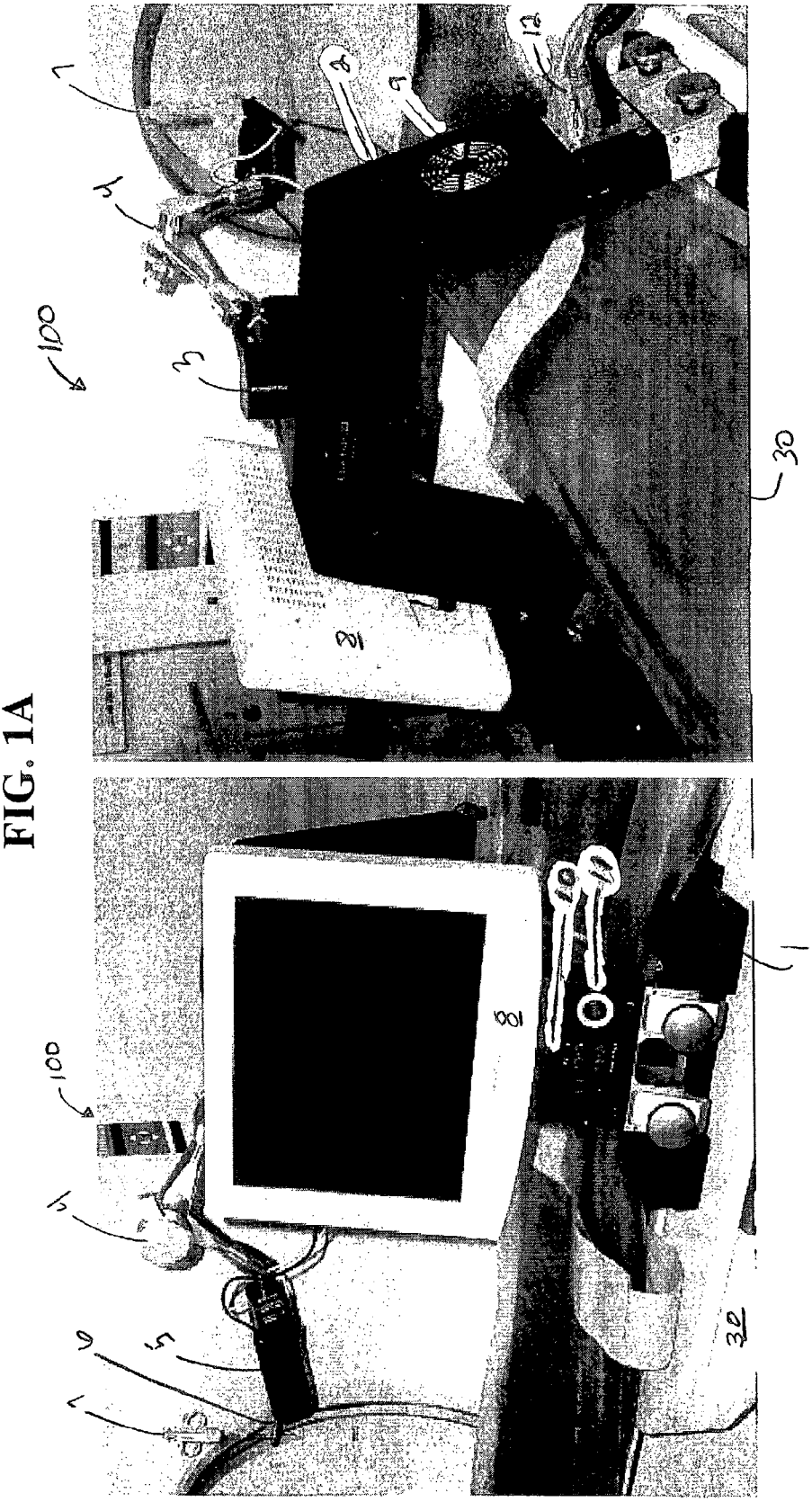
FIG. 1A is an illustration of a CT-guided intervention system according to an embodiment of the present invention.
Figure 1B:
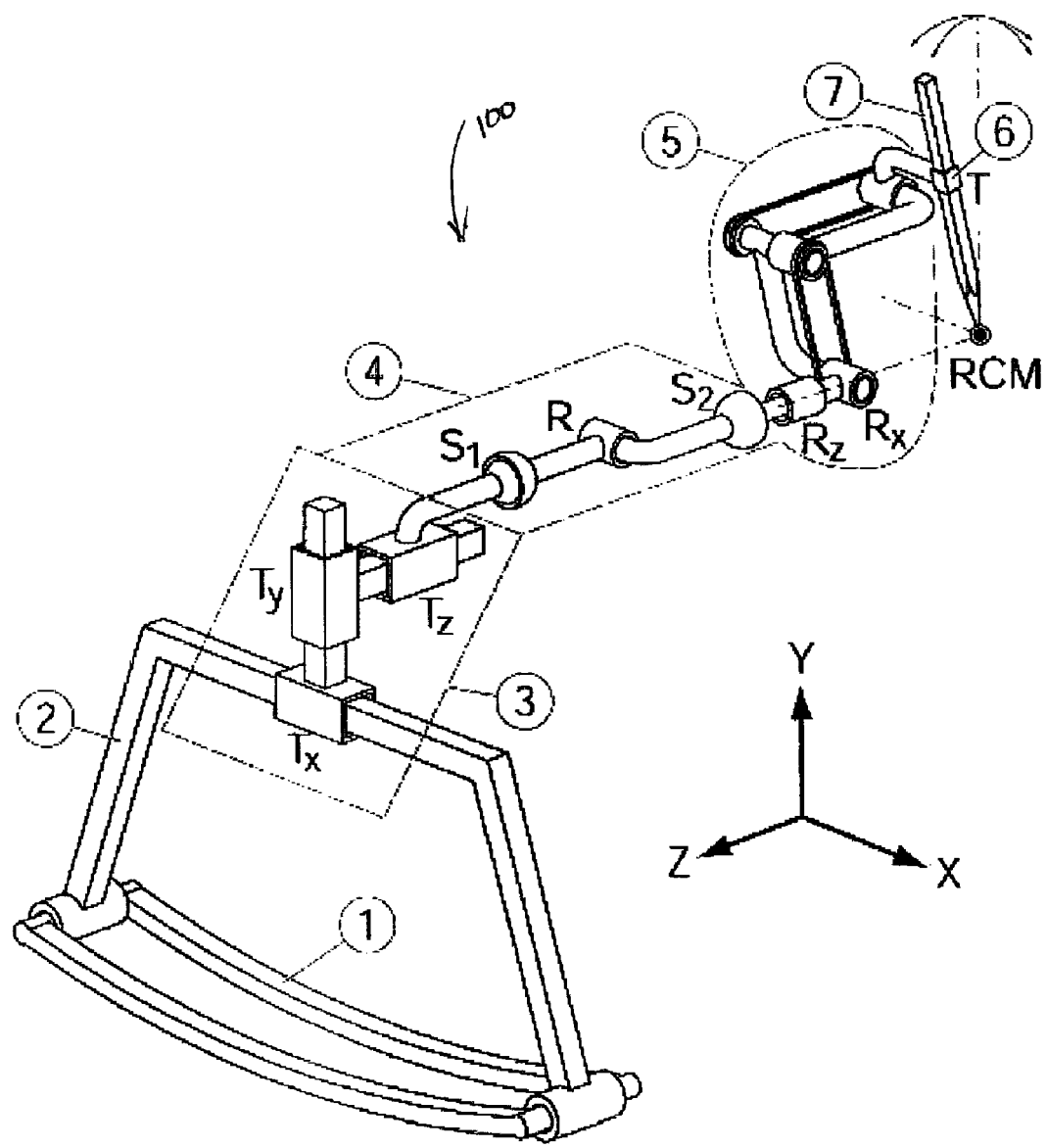
FIG. 1B is a robot kinematics diagram of the system shown in FIG. 1A.
Figure 1C:
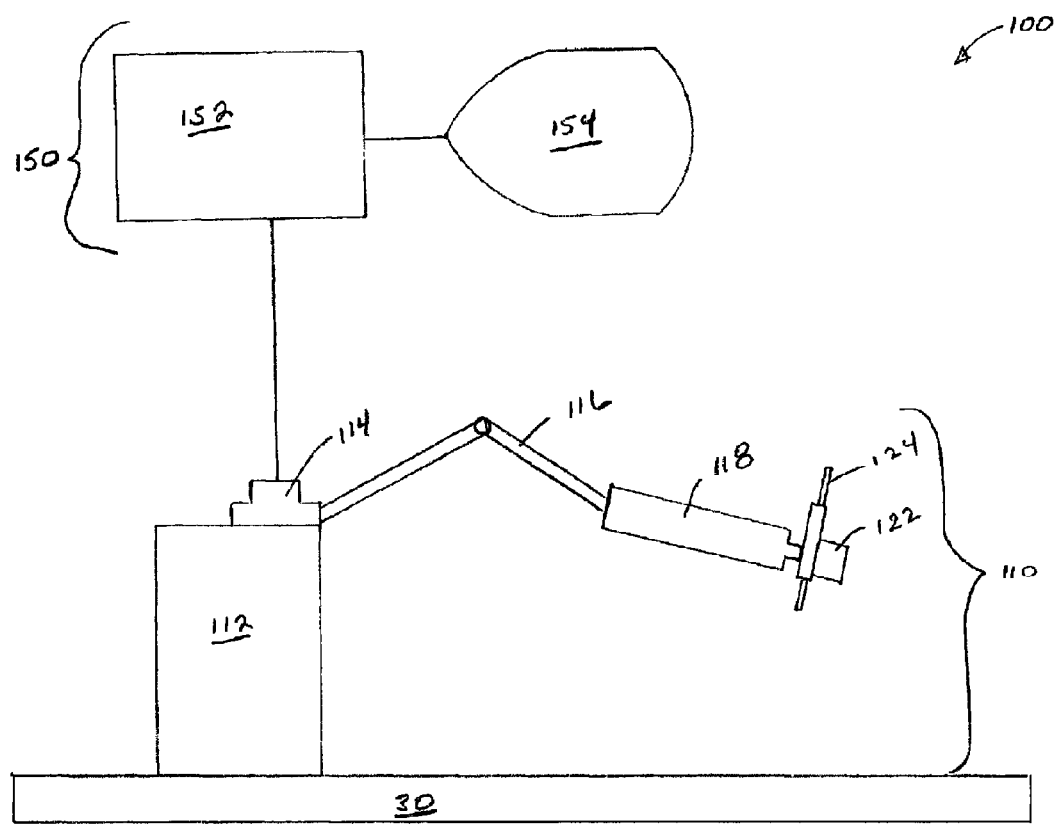
FIG. 1C provides an exemplary block diagram of an embodiment of present invention.

FIGS. 1A and 1B illustrate the current preferred embodiment of the CT-guided intervention system 100. FIG. 1C provides a block diagram for a second embodiment of the CT-guided intervention system 100. The CT-guided intervention system 100 includes a robot 110 connected to a control system 150.

The preferred embodiment of the robot 110 is formed from a bridge 2, 112; a XYZ module or positioning stage 3, 114; a passive positioning arm 4, 116; a RCM module 5, 118; and a PAKY driver 6, 122. In other embodiments, the robot may be formed from a base or support 112, a positioning stage 114, a passive positioning arm 116, a robot arm 118, and a instrument driver 122. The positioning stage 114 and passive positioning arm 116 may be optional with some configurations of robot arm 118. The robot 110 may be mounted to a CT table 30 that carries the patient. In the preferred embodiment, the robot is removablely mounted to CT table.

The base of the robot 2, 112 supports the positioning stage 3, 114. In the preferred embodiment the base 2, 112 presents a bridge-like structure over the table. The base 2, 112 may be fixed to the CT table 30 or may be attached to a table adapter 1. The preferred embodiment uses the table adapter 1.

The preferred adapter 1 is built to fit the scanner. The use of adapter 1 enables the robot to be used with different scanners by using different adapters 1. The preferred adapter 1 presents a thin structure following the top curvature of the table 30 and may be fastened to the table 30 by straps underneath the table 30. These straps may be formed from two flat bands. This type of mount is preferred since it does not require modifications of the scanner table 30 and does not interfere with its axial motion. This mounting system also permits the adapter to be arbitrarily located along the table and allows the robot to be positioned as desired along the patient. The preferred adapter 1 uses two cylindrical supports on each side of the table to attach the bridge 2, 112.

Mounting the bridge on the CT table of the preferred embodiment gives a convenient and sturdy support in close proximity to the patient. This mounting arrangement also preserves the relative positioning of the robot with respect to the patient during scanning. Its structure and movable location provides flexibility in performing interventions at any location of the body. The preferred adapter/bridge design makes the robot adaptable to any CT scanner.

In the preferred embodiment, the robot is mounted to the CT table 30. This mounting location permits the patient to be removed from the scanner during instrument insertion. In other embodiments the robot may be mounted to the floor, the wall, the ceiling, the scanner, or any other suitable location that permits the intervention system 100 to insert instrument 7, 124 to the target position with the required/desired accuracy. Other embodiments may employ any fixed or removable base and mounting system that has sufficient strength and rigidity to enable the intervention system 100 to insert instrument 7, 124 to the target position with the required/desired accuracy.

The positioning stage 3, 114 is carried by base 2, 112. In the preferred embodiment the positioning stage is a XYZ module that is fixed to the bridge 2 around its top member. The preferred XYZ module implements translation in the X, Y, and Z directions with (200 mm, 50 mm, 50 mm) travel respectively. In other embodiments, the positioning stage may provide translation in one or two directions. These translational stages may use classic ball-screws and linear-slides. Typically these stages are designed for the loads, travel, speed and compactness desired for the CT application. Some embodiments may not use/require a positioning stage 3, 114. The use of an accurate positioning stage permits adjusting the entry point of the instrument after registration of the instrument without re-registration of the instrument.

In the preferred embodiment the base of the passive positioning arm 4, 116 is mounted in the positioning stage 3, 114. In other embodiments the positioning arm 4, 116 may be carried by base 2, 112. The preferred positioning arm 4, 116 provides 7 degrees of freedom (spherical-cylindrical-spherical) and may be positioned and rigidly locked from a single lever. Other embodiments may employ a positioning arm with fewer degrees of freedom or that uses multiple levers to position and lock the positioning arm. The preferred arm 4, 116 makes it easier for an operator to position the instrument 124 at the insertion point since a single lever will lock the arm in position. An example of the positioning arm 4, 116 is the S-arm developed by Johns Hopkins.

The preferred embodiment employs an RCM module 5, 118 that is supported by the passive positioning arm 4, 116. This module presents six degrees of freedom (DOF) configured for decoupled positioning, orientation, and instrument insertion. In other embodiments, a robot arm or module 118 that permits the intervention system 100 to insert instrument 7, 124 to the target position with the required/desired accuracy may be used.

The RCM module 5, 118 [Stoianovici D, Whitcomb L L, Mazilu D, Taylor R H, Kavoussi L R: inventors; Johns Hopkins University assignee: Adjustable Remote Center of Motion Robotic Module. U.S. Provisional Patent 60/354,656. Filed Feb. 6, 2002 and Remote Center of Motion Robotic System and Method, U.S. patent application Ser. No. 10/359,284, filed Feb. 6, 2003; and Stoianovici D, Whitcomb L L, Anderson J H, Taylor R H, Kavoussi L R: A Modular Surgical Robotic System for Image Guided Percutaneous Procedures, (1998) LNCS, Springer-Verlag, 1496:404-410] is a small robotic module capable of precisely orienting a surgical instrument about two directions coincident at the RCM point. The preferred RCM module 5, 118 uses a new generation of the RCM robot that includes the "Ball-Worm" transmission [Stoianovici D, Kavoussi L R: inventors; Stoianovici D, Kavoussi LR assignee: Ball-Worm Transmission. U.S. Provisional Patent 60/339,247, PTC Application Filed Oct. 16, 2002], the BW-RCM. This version also includes redundant encoding and index counts. These significantly enhance the safety, kinematic performance, and rigidity of the RCM mechanism.

In the preferred embodiment, PAKY 6, 122 is mounted to the RCM module 5 so that the tip of the needle 7 is initially located at the RCM point. In other embodiments, an instrument driver 122 is carried by the robot arm 118.

PAKY 6, 122 is a sterilizable, radiolucent needle driver used to guide and actively drive a needle in percutaneous procedures [Stoianovici, D., Cadedu, J. A., Demaree, R. D., Basile H. A., Taylor, R. Whitcomb, L. L., Sharpe, W. N. Jr., Kavoussi, L. R.: "An eficient Needle Injection Technique and Radiological Guidance Method for Percutaneous Procedures", 1997 CVRMed-MrCas, Lecture Notes in Computer Science, Springer-Verlag, Vol. 1205, pp. 295-298, 1997]. PAKY 6, 122 tightly holds the needle and uses a rolling dowel mechanism to create a friction transmission system that allows needle advancement. An electric motor actuates needle insertion through a "Friction Transmission with Axial Loading" [Stoianovici D, Kavoussi L R, Whitcomb L L, Taylor R H, Cadeddu J A, Basile H A, Demaree R D, (1996): "Friction Transmission with Axial Loading and a Radiolucent Surgical Needle Drive", U.S. Patent Application No. 60/038, 115].

In other embodiments, any sterilizable, radiolucent instrument driver 122 that can insert instrument 124 to the target position with the required/desired accuracy may be used. In some embodiments, instrument driver 122 may not be sterilizable and/or radiolucent. In these embodiments the instrument driver should insert a sterilizable or sterilizable and radiolucent instrument 124.

Figure 6:
FIG. 6 shows a close-up view of the sterilizable, radiolucent needle holder (arrow) of the robot.

In the preferred embodiment, the instrument 124, represented by the biopsy needle 7, 124, is loaded in the PAKY driver 6, 122. FIG. 6 shows a close-up view of the preferred sterilizable, radiolucent needle holder 6, 122 of the robot 110. This needle holder 6, 122 creates no scatter artifact on the image. The needle 7, 124 is advanced by a rolling mechanism that propels the needle in forward and reverse directions.

In other embodiments, other instruments 124 may be carried by the instrument driver 122. Examples of these instruments include, but are not limited to, biopsy needles, RF ablation probes, cryotherapy devices, nephrostomy tubes, and neobladder access devices.

The needle holder 6, 122 and/or instrument driver 122 can accommodate any size needle 7, 124 and/or instrument 124. While eighteen gauge core biopsy needles and fifteen gauge RF devices were used in the interventions discussed below, any size needle 7, 124 or instrument 124 could be used.

In the preferred embodiment, needle 7, 124 and/or instrument advancement can be computer controlled in which the robot 110 is registered with-the CT image (see description below for registration method). This embodiment also provides a manual joystick control. The physician may use the manual control and the live CTF images to "drive" the needle to the target with the joystick. Preferably, there are two joystick controls. One joystick controls the forward-reverse advancement and the other joystick controls the trajectory orientation. Separating these two functions allows for increased safety. In other embodiments, only the manual control or computer control may be provided.

In the preferred embodiment, control system 150 for robot 110 is formed from a control box 152, a display 154, and an input device (not shown). In some embodiments the display 154 may be integrated into control box 152. In other embodiments, the control box 152 and display 154 may be integrated into the scanner control system. The input device may be any computer input device that can enter a position/location or control the robot 110. Examples of the input device include, but are not limited to, a keyboard, mouse, joystick, track ball and/or stylus.

Figure 2:
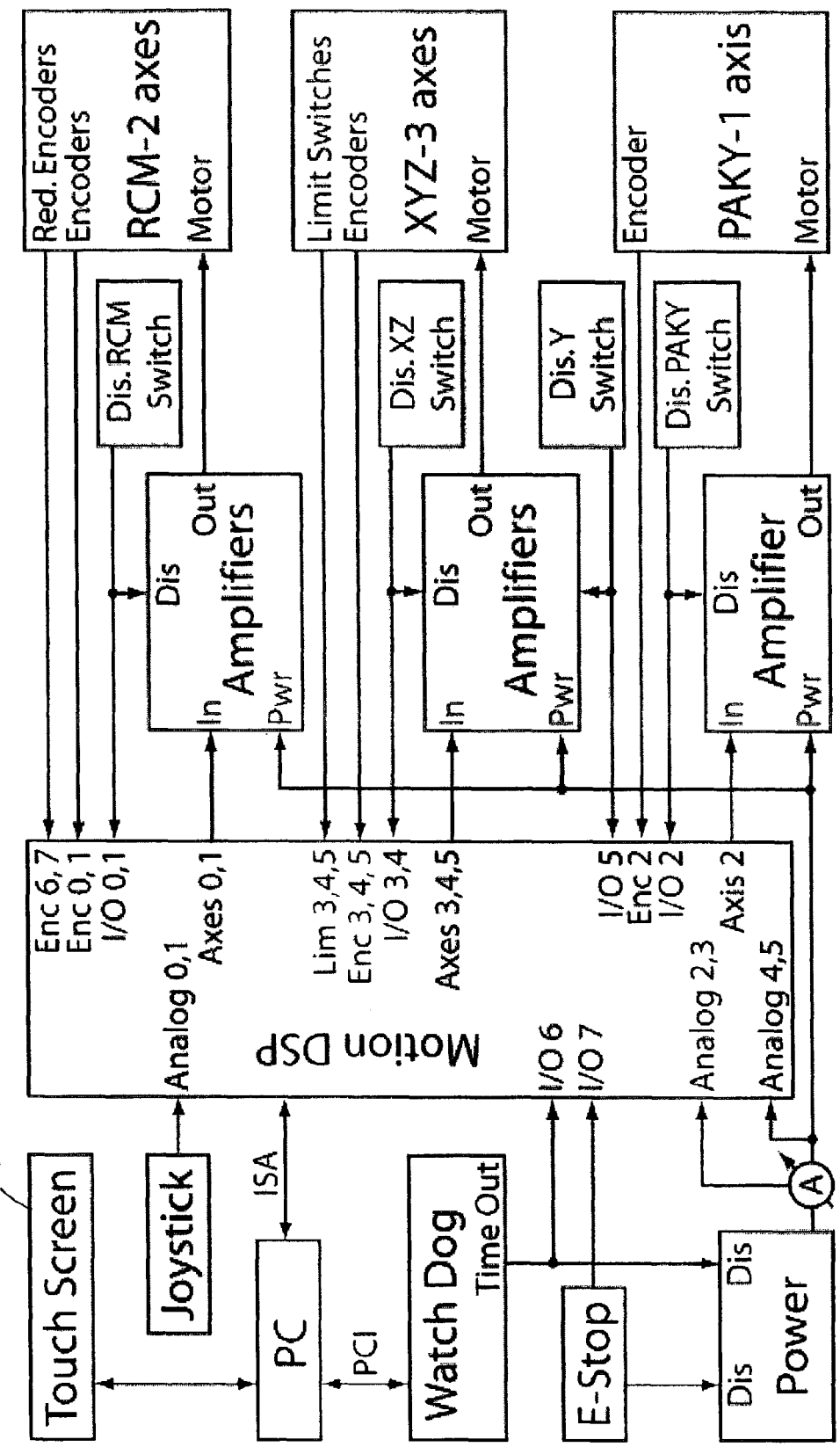
FIG. 2 is an functional block diagram the control system used in the embodiment of the present invention shown in FIG. 1A.

FIG. 2 illustrates the preferred embodiment of the control system 150. In the preferred embodiment, the control of the robot 110 is housed entirely within a single Industrial PC chassis. This PC uses a Dual Pentium III, 800 MHz motherboard with onboard network and video adapters, and standard HD, FD, CD components. On-board motion control is implemented by an 8-axis ISA-DSP card, PCX-DSP8 by Motion Engineering Inc. A relay board, CIO-ERB24 by Computer Boards Inc., is used for redundant enabling and disabling of the axes and power switches. Current sensors (LTS 6-NP by LEM USA) are also included for monitoring purposes. The motion control card commands 8 linear amplifiers, 4-Q-DC by Maxon Precision Motor Inc, powered by two 24V DC supplies.

Even though only 6 axes are used in the present version, the control box is configured for 8 axes to accommodate future developments of the instrument driver.

Other embodiments of the control box 152 may use different components as long as the control box 152 can cause robot 110 to insert instrument 7, 124 to the target position with the required/desired accuracy. Different configurations of robot 110 may also use different configurations or components for control box 152. Given the description of the preferred control box 152 and preferred robot 110, a person of ordinary skill would be able to construct embodiments of control box 152 suited to the particular robot 110 used in a particular application.

In the preferred embodiment display 154 is a resistive touch screen 15" monitor 8 that is conveniently mounted on the front side of the bridge 2. In other embodiments the display may be a standard monitor or a LCD screen. In the preferred embodiment the joysticks, switch panel 10, and an emergency switch 11 are also conveniently mounted on the front side of the bridge 2. A speaker 9 and the connectors for the cable 12 may be located on the back side of bridge 2. In other embodiments, display 154, joysticks and/or other control devices, switch panel, emergency switch, speaker 9 and the connectors for the cable 12 may be located wherever convenient. Some embodiments may not require and/or use a switch panel, emergency switch, or speaker.

Procedural Method and Safety Features

In the preferred embodiment, the mounting adapter 1 is initially attached to the mobile table 30 of the CT so that the PAKY 6 or instrument driver 122 will be near the procedure site. The robot 110 is then attached to the adapter. The patient is loaded from either side of the table by opening the bridge 2, 112 and tilting it on the opposite side. A sterile PAKY needle driver 6, 122 and the procedure needle 7, 124 are mounted so that the needle tip is at the RCM point. The passive arm 4, 116 is manipulated and locked in close proximity to the intervention site. Registration and imaging are performed next, according to the method of choice.

A person skilled in the art, based on the above description, should be able to setup other embodiments of the CT-guided intervention system 100.

The preferred embodiment uses a laser registration method [Patriciu A, Solomon S, Kavoussi L R, Stoianovici D, (2001): "Robotic Kidney and Spine Percutaneous Procedures Using a New Laser-Based CT Registration Method", LNCS, Vol. 2208, pp. 249-258]. This registration method aligns the procedure needle 7, 124 and/or instrument 124 using the laser markers of the CT scanner. Other embodiments may use other registration methods, for example, a localization device such as a Brown-Roberts-Wells frame or other localization device or method.

The skin entry point and the target are then selected within the same or different CT slices. In the preferred embodiment, the radiologist accesses the system from either the touch-screen monitor 8, 154 next to the patient or from a second input device directly attached to the computer located in the imager's control room. The radiologist identifies the location of the radiolucent portion of system 100 in a CT slice using a mouse or other computer input device. Similarly, the radiologist identifies the target location in the same or a different CT slice. Using the instrument driver registration, the location of the radiolucent portion, and the target location the control system 150 then controls the robot 110 to accurately insert instrument 124 to the target.

In the preferred embodiment, the XYZ stage 3, 114 is used to place the tip of the needle at the selected skin entry point. Then the RCM module 5, 118 or robot arm 118 orients the needle about its tip to the proper orientation to reach the target point. Thereafter, the PAKY 6, 122 or instrument driver 122 performs the insertion.

Other embodiments may use different processes to accurately insert instrument 124. The actual process used will depend on the particular configuration selected for robot 110 and control system 150.

The preferred embodiment includes optional safety features that are mechanical and control based. The robot 110 has decoupled motion capabilities corresponding to the needle manipulation sequence presented above. Accordingly, independent mechanisms are used to perform positioning, orientation, and insertion. This allows the control to sequentially enable-disable the moving element. Thus, only the active group may enabled in each sequence. For example, this insures that the needle is not inadvertently inserted during the orientation phase. Enable amplifier signals and redundant relays on the motor lines controlled from dedicated IO ports on the motion control card may be used for this purpose.

The preferred system 100 also includes an optional watchdog program that monitors the activity of the CPU control program, the state of the power voltages and currents, the state of the bypass disable buttons and the emergency switch located on the bridge panel. Every 100 ms this watchdog control program updates the register of a countdown timer. If not updated the counter sets its IO pin low which turns off power to the robot. All axes of the preferred embodiment of the robot 110 are non-backdrivable ensuring that the robot 110 will lock should an emergency stop or power loss occur.

In the preferred embodiment the size of the robotic components deployed inside the gantry is minimized without loss of maneuverability. This functionality is achieved by keeping the XYZ stage distal and using only the unrestricted orientation RCM module and the PAKY insertion stage inside the scanner. The system 100 control process is simple yet safe. Multiple activity monitors, emergency measures, and mechanical features ensure that the robot 110 can be immediately stopped still.

In other embodiments, the functionality provided may be determined by the actual components used.

Robot Accuracy Testing

In order to verify the accuracy of the preferred embodiment, a model was constructed with twenty-two 1-mm nipple markers dispersed throughout a three-dimensional phantom. The phantom was placed within the CT gantry, and the robotic arm holding an 18 g needle was positioned 5-10 cm from the nipple markers. After robot registration (see description below) images including the needle tip and each of the target markers were acquired. With a computer mouse the needle tip and the target point were defined for the control system 150. Then the robot 110 drove an eighteen gauge needle to a location near each marker.

Figure 3:
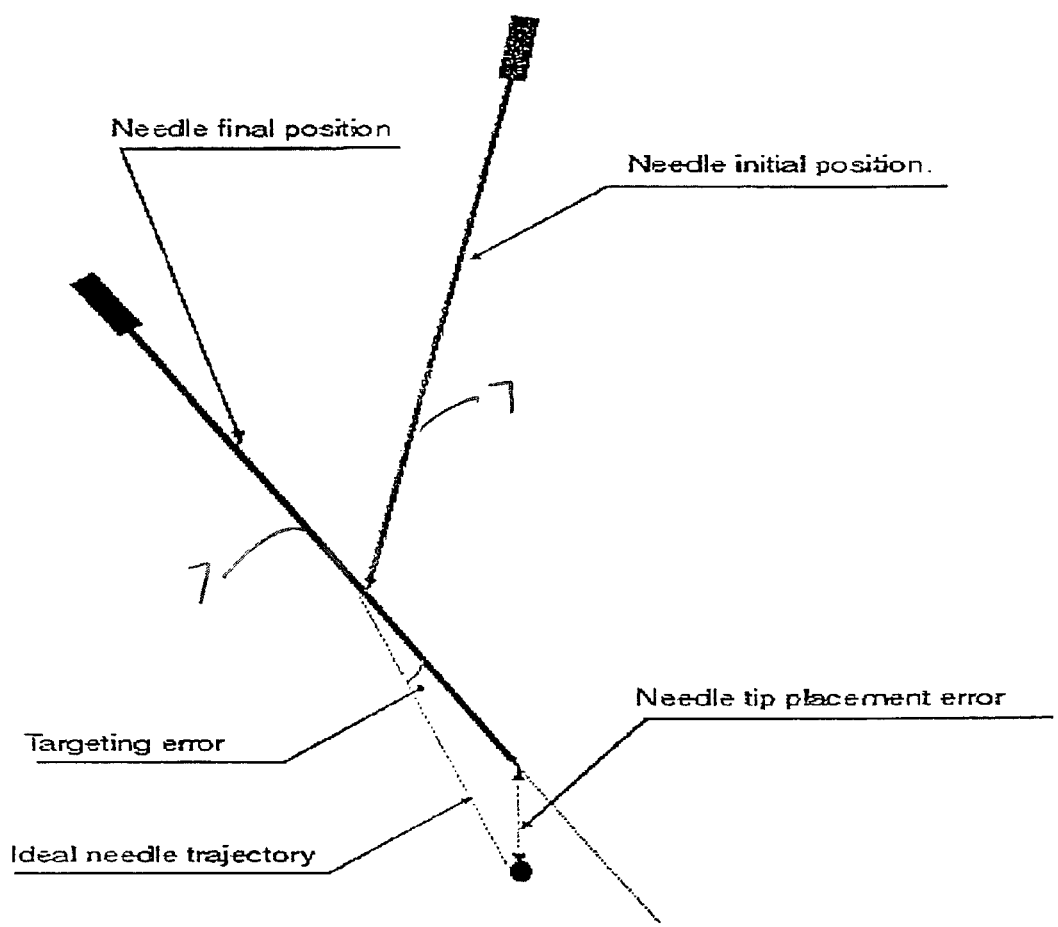
FIG. 3 shows an instrument at its initial position and at its final position as positioned by the present invention.
Figure 4:
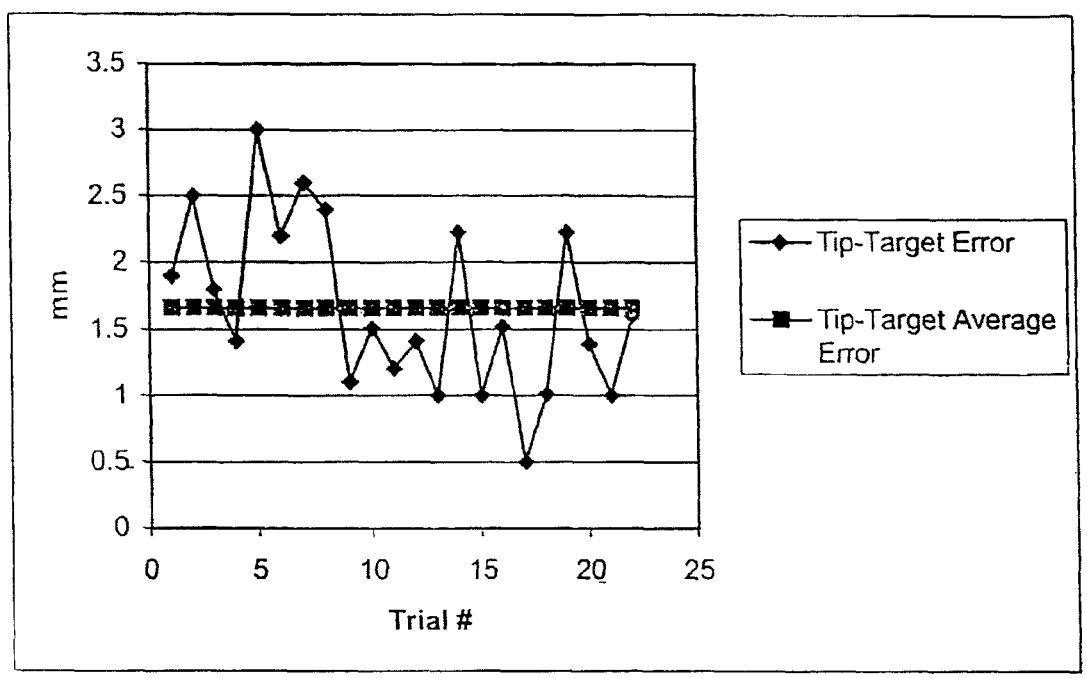
FIG. 4 illustrates the distance between the final needle tip position and the target (Tip-Target Error) for each of 22 individual attempts and an average distance.
Figure 5:
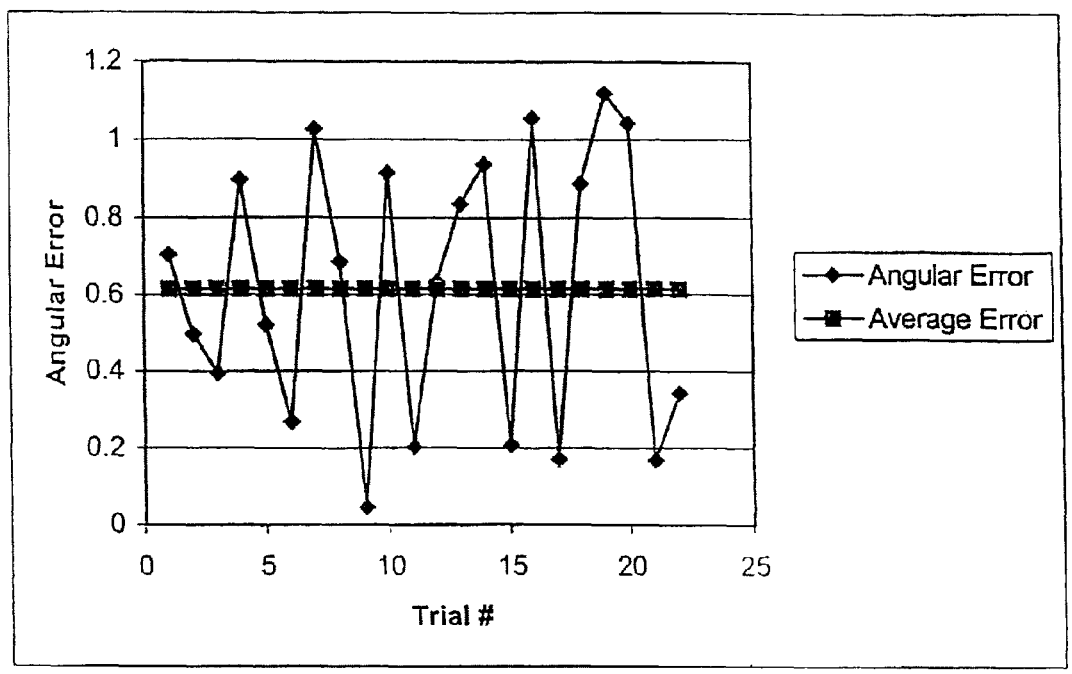
FIG. 5 illustrates the angular error, which indicates the difference between the ideal trajectory and the robot chosen trajectory for each of 22 individual attempts and the average error.

FIG. 3 shows the needle at its initial position and at its final position. The overall error is defined as the distance from the target to the tip of the needle after the robot had driven the needle to the target. The targeting accuracy is defined as the angle between the ideal trajectory and the actual trajectory of the needle after robotic alignment. from the target to the direction of the needle. FIGS. 4 and 5 illustrate the two accuracy measurements made for each test. FIG. 4 shows the overall error and FIG. 5 illustrates the targeting accuracy.

Patient Testing

After verifying the accuracy of the preferred embodiment in the phantom, tests were conducted on patients. Sixteen patients were scheduled for twenty-three CT guided procedures. The procedures included radiofrequency (RF) ablation (11), core needle biopsy (10), nephrostomy tube placement (1), and neobladder access (1). All patients provided informed consent under an IRB approved protocol aimed at testing feasibility and accurate targeting of the robot 110. As part of the patient evaluation, the size of the target and appropriate needle tip location were assessed by the one or two radiologists present to do the procedure.

Entry Site Selection

In order to select the entry site and plan the procedure, the patients were placed on the CTF table (Somatom Plus 4 with CARE Vision, Siemens, Iselin, N.J.). Patients were placed supine or prone depending on the-expected skin entry site. The patients' legs were slid into a frame that attached to the table and from which the robot arm extended. A non-contrast, spiral scan with a breath hold was obtained to localize the lesion and plan the procedure. The appropriate slice for needle entry was selected, and the table was moved to that position. Metallic nipple markers were placed on the patients' skin at the selected slice using the CT scanner laser light for guidance. Another single breath hold image at the selected slice was acquired. The nipple markers visible on the CT image allowed for selection of the appropriate skin entry site. Each patient's skin was cleaned with betadine and local lidocaine was administered over the planned entry site. A small dermotomy was made in the skin at the appropriate entry site.

Instrument Registration

A number of possible image registration methods are possible [Susil R C, Anderson J, Taylor R E: A Single Image Registration Method for CT Guided Interventions. MICCAI 1999, Lecture Notes in Computer Science, Springer-Verlag (1999) 1679:798-808]. The registration method used in this study took: advantage of the laser light incorporated in the slice selection of all CT scanners.

Figure 7A:
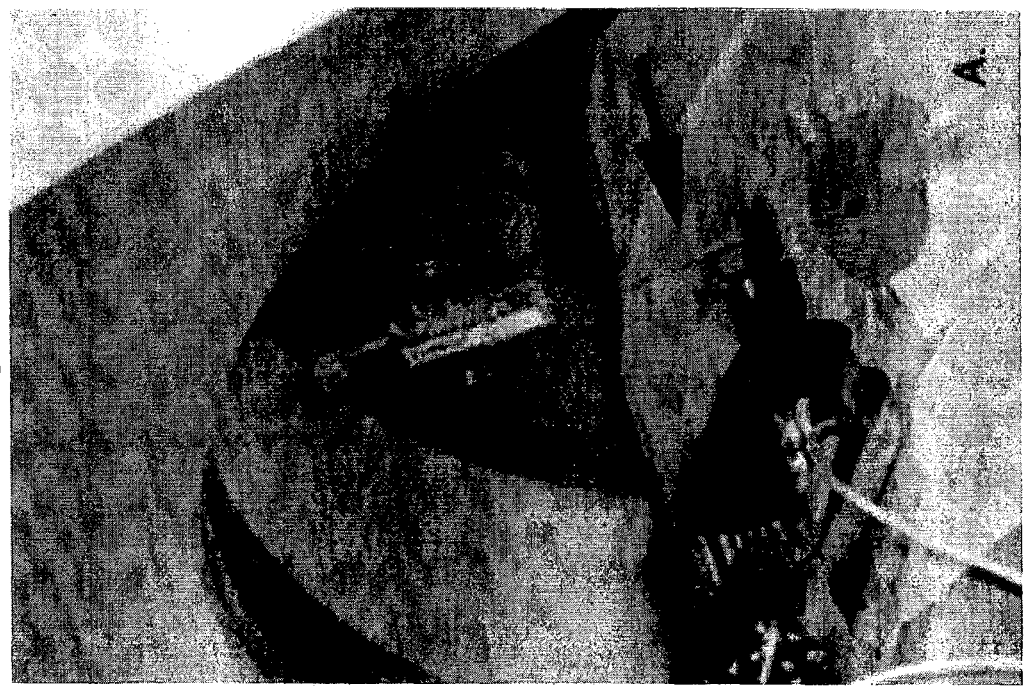
FIGS. 7A and B demonstrate the registration method for aligning the robot's coordinate system with the image coordinate system.
Figure 7B:
FIG. 7B shows again the reflection of the laser beam on the shaft but in a different position.

FIGS. 7A and B demonstrate the registration method for aligning the robot's coordinate system with the image coordinate system. This registration method uses the laser light plane of the CT scanner. FIG. 7A shows the needle in the plane of the laser-with reflection on the shaft (arrow). FIG. 7B shows again the reflection of the laser beam on the shaft but in a different position. These two positions define the slice plane. The third coordinate comes from the CT table position known by the CT scanner. A detailed discussion of this registration method may be found in U.S. patent application Ser. No. 10/367,953.

The passive arm 116, robot module 118, and instrument driver 122 holding the appropriate needle 7, 124 for the given procedure; were manually placed such that the tip of the needle was in the skin dermotomy site. The needle shaft was moved to reflect the CT laser light. This point was noted by the control system 150. Then a second position with the needle tip still in the entry site-was selected. This second position was selected to also reflect the laser light along the needle shaft. The second position was noted by the control system 150. Thus the two needle positions reflecting the laser light were used to identify a plane for image registration. The third coordinate comes from the table position of the CT scanner.

Target Selection

To select the target, a breath hold single image was taken showing the tip of the needle. The image was transferred to the control system 150. The tip of the needle and shaft were indicated to the control system 150 by the physician using a computer mouse. Then, a breath hold image was taken showing the target. This was not always the same image that showed the needle tip. The image was transferred to the control system 150 and the target position was again indicated with the computer mouse.

FIGS. 8A and B show examples of two images sent to the computer workstation. FIG. 8A was used by the physician to indicate the tip of the needle at the skin and the holder of the needle. Small 'x' marks are indicated (arrows). These marks indicate the needle tip and the shaft of the needle. FIG. 8B was used to indicate the target. In this-example the target is in the same image as the needle tip, but it need not be. In this image an 'x' mark is indicated at the target (arrow), an exophytic renal mass.

Robot Needle Insertion

The preferred robot 110 first moved the needle to the correct trajectory, and then under CTF (50 mA, 120 kVp) the robot advanced the needle to its target location without physician radiation exposure. This was done during breath hold and under CTF guidance. The target was the mass for the core biopsies, the collecting system for the nephrostomy tube and the neobladder for the neobladder access procedure. In the case of the RF ablations, the robot moved to the correct: angle for placement but did not-advance the probe. The ablation probe was manually pushed to the correct depth. This was done manually since the PAKY 6, 122 used was found to strip the insulation off the RF probe. Manual advancement was performed using the "spot-check" method of CTF. Joystick control was used if fine-tuning of position was necessary. This occurred in cases of respiratory motion where the lesion moved in and out of the target coordinates. The joystick control combined with CTF imaging allowed advancement of the needle to be timed with the respiratory motion.

Procedure Assessment

The procedures were assessed by CT imaging of the needle tip in the target tissue. In addition for the cases of the neobladder access and the nephrostomy tube placement urine return was evidence of successful targeting. Pathologic reports were correlated with imaging findings for the ten robotic biopsy cases.

In Vitro Results

As shown in FIG. 5, the phantom studies showed a mean angular error of 0.61 degrees. The mean angular error is the error angle between the ideal trajectory to the target and the robot's actual selected trajectory. The results of the phantom studies illustrated in FIG. 4 show a mean distance error between the target and the ultimate needle tip position of 1.66 mm.

Patient Results

All interventional procedures were successfully performed without complication. These procedures included 10 percutaneous core biopsies (kidney-7, lung-2, liver-1), 11 radiofrequency ablations (kidney-9, spine-2), 1 nephrostomy tube placement, and 1 neobladder access. FIGS. 9A, B and C show examples of these three CT interventional procedures. FIG. 9A shows the robot positioned for a percutaneous biopsy. FIG. 9B shows the robot positioned for an RF ablation. FIG. 9C shows the robot positioned for a nephrostomy tube placement. The physician in the room is finishing the procedure with the working site outside of the gantry.

A summary of the procedures and the corresponding results is provided in Table 1 below. In each case success was defined as hitting the target correctly with the needle tip. Target size ranged from 1.0 cm for a biopsy lesion to 8.0 cm for the neobladder. In four cases the needle did not adequately meet the target and required fine-tuning adjustment with joystick control to ultimately reach the target. These were the patient numbers 1, 3, 8, and 14 for which the targets were 2.5, 1.0, 2.0, and 2.0 cm respectively. The remainder were satisfactorily targeted based on imaging interpretation.

TABLE 1

| Patient Number | Target | Findings | Largest Diameter |
| --- | --- | --- | --- |
| 1 | Kidney Biopsy | Atypia | 2.5 cm |
| 2 | Nephrostomy | Urine | 5.0 cm |
| 3 | Kidney Biopsy and RF Ablation | Atypia | 1.0 cm |
| 4 | Two Spine RF Ablations | - | 3.0 cm and 2.5 cm |
| 5 | Kidney RF Ablation | - | 2.5 cm |
| 6 | Kidney Biopsy and RF Ablation | Focal Scarring | 2.5 cm |
| 7 | Neobladder Access | Urine - | 8.0 cm |
| 8 | Kidney Biopsy and RF Ablation | Inflammation | 2.0 cm |
| 9 | Kidney Biopsy and RF Ablation | Inflammation | 2.0 cm |
| 10 | Kidney Biopsy and RF Ablation | Atypia | 2.5 cm |
| 11 | Liver Biopsy | Neoplasm | 3.0 cm |
| 12 | Kidney RF Ablation | - | 2.5 cm |
| 13 | Lung Biopsy - | Non-Small Cell Lung Cancer-' | 3.0 cm |
| 14 | Lung Biopsy | Plasma Cells, Fibroblast Proliferation, and Granulation Tissue | 2.0 cm |
| 15 | Kidney RF Ablation | - | 2.0 cm |
| 16 | Muscle Biopsy and RF Ablation | Leiomyosarcoma | 2.0 cm - |

The above data illustrates that the preferred embodiment of system 100 can hold and advance the needle with sufficient accuracy. Since the physician's hands do not need to be in the scanning plane at all, physician radiation exposure can be dramatically reduced.—In fact, radiation exposure to the physician can be completely eliminated if the joystick and computer are placed in the control room where the physician can view the technologist's monitor to perform the procedure.

Radiation exposure to the patient can be reduced with use of the system 100 as well. Since the computer 152 can reliably drive the robot's needle 124 to the target, continuous imaging may not be necessary as long as respiration is relatively controlled. This will significantly reduce patient radiation exposure. This method of allowing the computer 152 to drive the needle 124 without continuous CTF imaging may also be useful in cases where the CTF modality is not available.

Once the robot finishes driving the needle a subsequent image may be acquired to assess needle position. Any inaccuracies in registration- or movement due to respiration can be updated with the joystick manual control.

One of the challenges in standard CTF procedures is that the entry site may not be in the same plane as the lesion. Multiple manual manipulations are often necessary to determine the correct needle trajectory. In system 100, this challenge can be avoided. The needle tip/entry site for registration and the lesion can be in different scan planes. The ability to have the computer 152 drive the needle tip to the plane of the lesion can avoid having to "hunt" for the needle tip.

Use of the robot may limit the tactile feel that an interventionalist often times relies on in performing procedures. Many researchers have applied haptic interfaces to simulate the force feedback that a physician may sense in doing a procedure such as angioplasty or laparoscopy [Barnes S Z, Morr D R, Oggero E, Pagnacco G, Berme N. The realization of a haptic (force feedback) interface device for the purpose of angioplasty surgery simulation. Biomed Sci Instrum 1997; 33:19-24 and Baur C, Guzzoni D, Georg O. VIRGY: a virtual reality and force feedback based endoscopic surgery simulator. Stud Health Technol Inform 1998; 50:110-6]. These interfaces have been focused on virtual reality educational simulations. Some of these techniques may be incorporated into the joystick control of the robot 110.

The intervention system 100 may also be useful in standard CT scanners without CTF. In these cases the robot 110 can advance the needle to the target without the repeated scanning and "hunting" for the needle tip that occurs in conventional procedures. This can potentially save procedure time and may improve accuracy.

Several instruments including interventional tools such as RF devices may not fit well into the CT gantry. A short needle may be used to "register" the robot for the correct trajectory, and then out of the CT gantry the appropriate instrument 124 is placed into the robot 110 and driven to the target.

Although the invention has been described based upon the preferred embodiment, it would be apparent to those of skilled in the art that certain modifications, variations, and alternative constructions would be apparent, while remaining within the spirit and scope of the invention. In order to determine the metes and bounds of the invention, therefore, reference should be made to the appended claims.

For example, the system and method of the present invention may be implemented in urology as well as other medical fields. The system and method may also prove useful for applications involving similar imaging equipment, for example Single plane or Biplanar X-Ray Fluoroscopy.

All references cited in this patent application are herein incorporated by reference, each in its respective entirety.

We claim:

1. A robotic system for computed tomography guided operations involving a patient, the system comprising:
    a radiolucent instrument driver positionable about a predetermined point located on the patient, wherein the radiolucent instrument driver is free of being mounted on the patient;
    a robot attached to a support bridge which spans an upper surface of a CT table onto which the patient is positioned in a direction which is orthogonal relative to a longitudinal axis of the CT table, the robot comprising:
        a positioning stage mounted on the support bridge that translates the radiolucent instrument driver in an x-plane, a y-plane, and a z-plane, and
        a robotic module that positions the radiolucent instrument driver about two directions to angularly orient the radiolucent instrument driver coincident the predetermined point;
    a control device connected to the robot and the radiolucent instrument driver comprising:
        means for generating a first signal, a robot control signal, and a driver control signal, wherein the control device is configured to perform a medical device manipulation sequence that sends the first signal to the positioning stage to translate the radiolucent instrument driver proximate the predetermined point in the x, y, and z-planes, send the robot control signal to the robot that causes the robotic module to place the radiolucent instrument driver in a desired angular orientation with respect to the predetermined point, and, after the radiolucent instrument driver is in the desired orientation, the control device is further configured to send the driver control signal to the radiolucent instrument driver that causes the radiolucent instrument driver to insert a medical device attached thereto through the predetermined point to a location proximate a target point in the patient, and wherein the control device is further configured to maintain a relative positioning of the medical device with respect to the predetermined point on the patient; and
        means for decoupling the first signal, the robot control signal and the driver control signal so that each of the positioning stage, the robotic module and the radiolucent instrument driver are individually actuated sequentially in accordance with the medical device manipulation sequence.

2. The system of claim 1, further comprising a means for generating a first position signal and a second position signal, wherein the control device receives the first position signal to indicate the location of the predetermined point and the second position signal to indicate the location of the target position, wherein the control device, based on the first and second position signals, automatically calculates the desired orientation for the radiolucent instrument driver and a distance to the target point, and wherein the control device, based on the calculated orientation and distance, sends the robot control signal and the driver control signal.

3. The system of claim 2, further comprising at least one image provided to the control device, wherein the first and second position signals are based on the at least one image.

4. The system of claim 1, wherein the control device further comprises at least one joystick that generates at least one joystick control signal, and wherein the robot control signal and the driver control signals are based on the at least one joystick control signal.

5. The system of claim 1, further comprising a single frame of reference determined relative to the robot and a scanning direction of the patient, wherein the single frame of reference is maintained by the control device.

6. The system of claim 1, wherein the medical device is a needle.

7. The system of claim 1, wherein the medical device is a RF ablation device.

8. The system of claim 1, wherein the control device is a computer and a display.

9. The system according to claim 1, wherein the support bridge is tiltable relative to the upper surface of the CT table.

10. The system according to claim 1, wherein the support bridge is attached to one of the CT table and a table adapter.

11. The system according to claim 10, wherein the table adapter is configured to span the upper surface of the CT table and comprises at least one strap that extends underneath the CT table and affixes the table adapter to the CT table.

12. The system according to claim 11, wherein the table adapter is configured to span the upper surface of the CT table and comprises at least one strap that extends underneath the CT table and affixes the table adapter to the CT table.

13. A robotic system for computed tomography (CT) guided operations involving a patient, the system comprising:
    a support bridge mounted to a CT table on which the patient is positioned, wherein the support bridge spans a top surface of the CT table in a direction which is orthogonal relative to a longitudinal axis of the CT table;
    an XYZ module carried by the support bridge;
    a passive arm connected to the XYZ module;
    a RCM robot module connected to the passive arm;
    a PAKY radiolucent needle driver carried and positioned by the robot module;
    a control device configured to control positioning of the XYZ module, the needle driver and the robot module relative to a predetermined point located on the patient, wherein the XYZ module, robot module and needle driver are free from being mounted on the patient, wherein the control device is configured to perform a medical device manipulation sequence that outputs a first signal to the XYZ module that controls the position of the XYZ module, output a second signal to the robot module that controls the angular orientation of the needle driver, and output a third signal to the needle driver that controls and maintains a relative positioning of a medical device attached to the needle driver with respect to the predetermined point on the patient during a CT guided operation; and means for decoupling control of the position of the XYZ module, control of the angular orientation of the needle driver, and control of the relative positioning of the medical device, wherein each control is individually actuated sequentially in accordance with the medical device manipulation sequence.

14. The system according to claim 13, further comprising a single frame of reference determined relative to the robot and a scanning direction of the patient during a CT guided operation, wherein the single frame of reference is maintained by the control device.

15. The system according to claim 13, wherein the CT table is one of stationary and fixed in position.

16. The system according to claim 13, wherein the support bridge is tiltable relative to the upper surface of the CT table.

17. The system according to claim 13, wherein the support bridge is attached to one of the CT table and a table adapter.

18. A system for computed tomography (CT) operations involving a patient, the system comprising:

positions means for positioning a tip of a medical device at an insertion point, wherein the positions means is attached to a support bridge which spans a top surface of a CT table onto which the patient is positioned in a direction which is orthogonal relative to a longitudinal axis of the CT table;

registration means for registering the medical device;

orientating means for orientating the medical device to an angular orientation required to insert the medical device through the insertion point and position the tip of the medical device proximate a target;

inserting means for inserting the medical device through the insertion point to a point where the tip of the medical device is proximate the target, wherein the positions means, the registration means, the orientating means and the inserting means are free from being mounted on the patient, and wherein the orienting means maintains a relative positioning of the medical device with respect to a predetermined point on the patient during a CT guided operation; and decoupling means for providing independent control of each of the positions means, the orientating means and the inserting means in accordance with a medical device manipulation sequence, wherein each motion of positioning the tip of the medical device, orienting the medical device, and inserting the medical device is individually actuated sequentially by a control device in accordance with the medical device manipulation sequence.

19. The system of claim 18, wherein the orientating means comprises:

identifying means for identifying a position of the tip of the medical device and for identifying a target;

calculating means for calculating the orientation of the medical device required to insert the medical device through the insertion point and position the tip of the medical device proximate the target; and positioning means for positioning the medical device in the calculated orientation.

20. The system of claim 18, wherein the medical device comprises a needle.

21. The system of claim 20, wherein the needle is a biopsy needle.

22. The system of claim 18, wherein the medical device comprises an RF ablation target.

23. The system according to claim 18, wherein the support bridge is tiltable relative to the upper surface of the CT table.

24. The system according to claim 18, wherein the support bridge is attached to one of the CT table and a table adapter.

25. The system according to claim 24, wherein the table adapter is configured to span the upper surface of the CT table and comprises at least one strap that extends underneath the CT table and affixes the table adapter to the CT table.

* * * * *